(12) United States Patent
Pai et al.

(10) Patent No.: US 7,872,154 B2
(45) Date of Patent: Jan. 18, 2011

(54) METHOD FOR THE PREPARATION OF 4-FLUORO-α-[2-METHYL-1-OXOPROPYL]-γ-OXO-N-β-DIPHENYLBENZENEBUTANAMIDE AND PRODUCTS THEREFROM

(75) Inventors: Ganesh Gurpur Pai, Thane (IN); K. Nanda Kishore, Hyderabad (IN); Narendra P. Chaudhari, Navi Mumbai (IN); N. Anjaneyulu, Medak District (IN); B. N. Ghogare, Gurgaon (IN)

(73) Assignee: Arch Pharmalabs Limited, Mumbai (IN)

( * ) Notice: Subject to any disclaimer, the term of this patent is extended or adjusted under 35 U.S.C. 154(b) by 0 days.

(21) Appl. No.: 12/255,764

(22) Filed: Oct. 22, 2008

(65) Prior Publication Data

US 2009/0298907 A1 Dec. 3, 2009

(30) Foreign Application Priority Data

May 29, 2008 (IN) ...................... 1152/MUM/2008

(51) Int. Cl.
C07C 233/05 (2006.01)
(52) U.S. Cl. ..................................... 564/169
(58) Field of Classification Search ................... 564/169
See application file for complete search history.

(56) References Cited

U.S. PATENT DOCUMENTS

| 4,681,893 | A |   | 7/1987 | Roth |   |
|---|---|---|---|---|---|
| 5,003,080 | A |   | 3/1991 | Butler et al. |   |
| 5,097,045 | A |   | 3/1992 | Butler et al. |   |
| 5,124,482 | A | * | 6/1992 | Butler et al. | ................. 564/169 |
| 5,216,174 | A |   | 6/1993 | Butler et al. |   |
| 2007/0249865 | A1 | * | 10/2007 | Mathew et al. | ............... 564/169 |

FOREIGN PATENT DOCUMENTS

| KR | 1020040001435 | 1/2004 |
|---|---|---|
| KR | 1020050012432 | 2/2005 |
| WO | 03/004457 | 1/2003 |
| WO | 2006/021968 | 3/2006 |

OTHER PUBLICATIONS

Pak et al., "Aminolysis of 5-Acyl-2,2-dimethyl-1,3-dioxane-4,6-diones (Acyl Meldrum's Acids) as a Versatile Method for the Synthesis of β-Oxo Carboxamides," Synthesis, 1992(12): 1213-1214 (1992).

Woo et al., "Atorvastatin, an HMG-COA reductase inhibitor and effective lipid-regulating agent. Part I. Synthesis of ring-labeled [14C] atorvastatin," Journal of Labeled Compounds Radiopharmaceuticals, 42(2): 121-127 (1999).

Yamamoto et al. "1,3-Oxazines and Related Compounds. XIII. Reaction of Acyl Meldrum's Acids with Schiff Bases Giving 2,3-Disubstituted 5-Acyl-3,4,5,6-tetrahydro-2H-1,3-oxazine-4,6-diones and 2,3,6-Trisubstituted 2,3,-dihydro-1,3-oxazin-4-ones," Chem. Pharm. Bull, 35(5):1860-1870 (1987).

Oikawa et al., "Meldrum's Acid in Organic Synthesis. 2. A General and Versatile Synthesis of β-Keto Esters," J. Org. Chem., 43(10): 2087-2088 (1978).

Sagyam R R; et al. "An efficient synthesis of highly substituted pyrrole and bis pyrrole derivatives," Journal of Heterocyclic Chemistry, Jul. 1, 2007, vol. 44, pp. 923-926.

* cited by examiner

*Primary Examiner*—Shailendra Kumar
(74) *Attorney, Agent, or Firm*—Akerman Senterfitt; Peter A. Chiabotti

(57) ABSTRACT

A method for the preparation of 4-fluoro-α-[2-methyl-1-oxopropyl]-γ-oxo-N-β-diphenylbenzenebutanamide also known as 2-[2-(4-fluorophenyl)-2-oxo-1-phenylethyl]-4-methyl-3-oxo-pentanoic acid phenylamide of the formula I containing about 0.1% or less of α-[2-methyl-1-oxopropyl]-γ-oxo-N-p-diphenylbenzene butanamide, about 0.05% or less of difluoro-α-[2-methyl-1-oxopropyl]-γ-oxo-N-β-diphenylbenzene butanamide and about 0.1% or less of 3-[2-(4-Fluorophenyl)-2-oxo-1-phenyl-ethoxy]-4-methyl-pent-2-enoic acid phenylamide.

6 Claims, 4 Drawing Sheets

FIG.1A | FIG.1B

Figures 1, 1A:
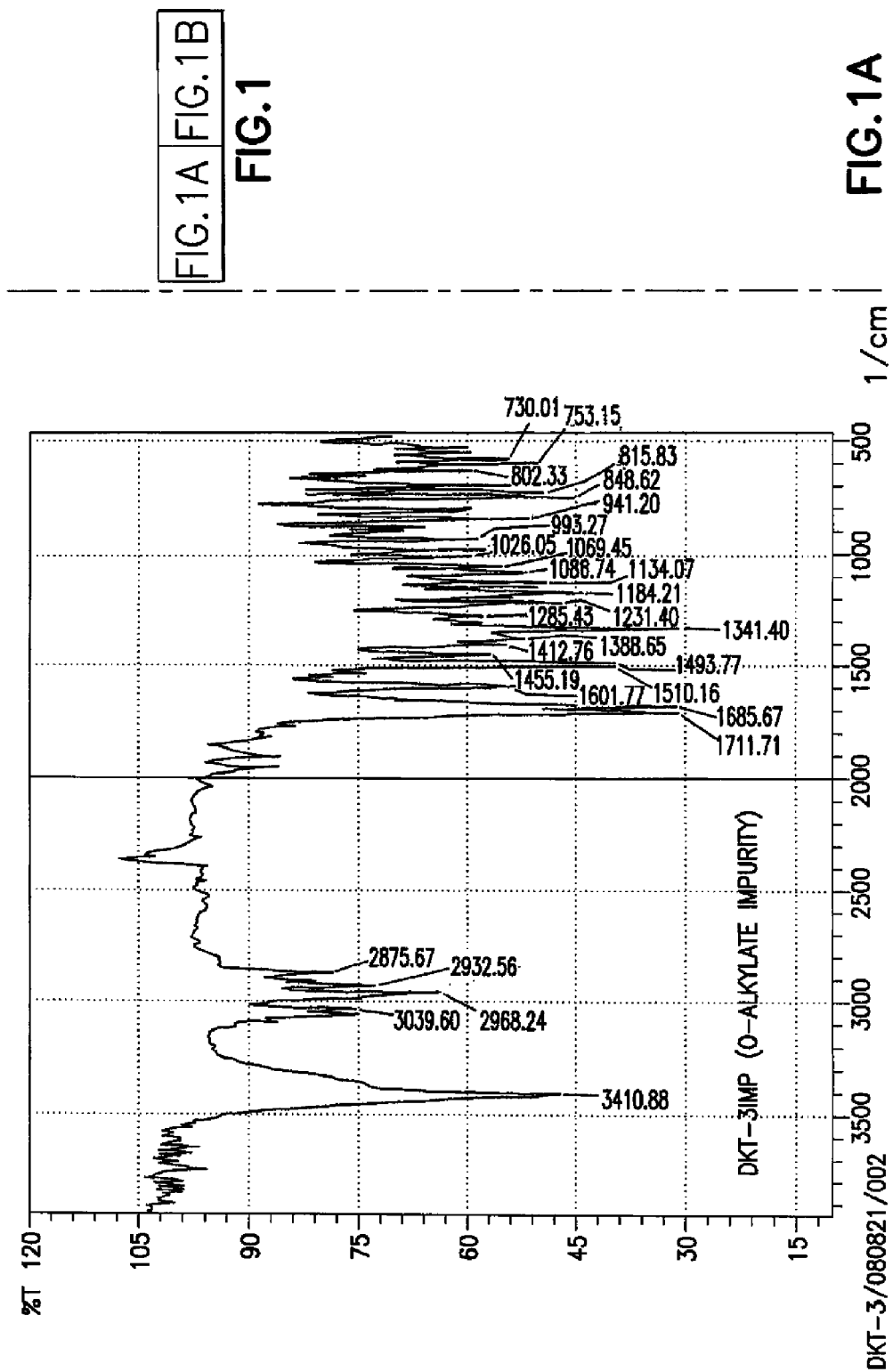

| No. | PEAK | INTENSITY | CORR. INTE | BASE (H) | BASE (L) | AREA | CORR. ARE |
|---|---|---|---|---|---|---|---|
| 1 | 528.46 | 59.791 | 10.236 | 536.17 | 520.74 | 2.881 | 0.493 |
| 2 | 549.67 | 60.68 | 9.64 | 559.32 | 536.17 | 4.227 | 0.687 |
| 3 | 578.6 | 55.141 | 14.811 | 593.07 | 560.28 | 6.679 | 1.601 |
| 4 | 602.71 | 50.675 | 17.665 | 611.39 | 594.03 | 3.9 | 1.028 |
| 5 | 629.72 | 62.189 | 13.11 | 649 | 622.96 | 3.527 | 0.622 |
| 6 | 697.22 | 42.319 | 32.582 | 706.86 | 686.61 | 5.127 | 2.597 |
| 7 | 730.01 | 52.547 | 29.916 | 739.65 | 720.36 | 3.293 | 1.678 |
| 8 | 753.15 | 45.377 | 36.058 | 766.65 | 739.65 | 4.966 | 2.556 |
| 9 | 802.33 | 60.043 | 14.122 | 808.12 | 782.08 | 3.162 | 0.47 |
| 10 | 815.83 | 51.392 | 22.072 | 832.23 | 808.12 | 4.328 | 1.346 |
| 11 | 848.82 | 47.874 | 34.918 | 878.52 | 832.23 | 8.927 | 3.308 |
| 12 | 941.2 | 55.988 | 24.981 | 960.48 | 924.8 | 5.728 | 2.474 |
| 13 | 993.27 | 57.15 | 18.87 | 1007.74 | 979.77 | 4.956 | 1.577 |
| 14 | 1026.06 | 62.23 | 11.344 | 1033.77 | 1019.31 | 2.473 | 0.522 |
| 15 | 1069.45 | 55.398 | 18.289 | 1079.1 | 1047.27 | 5.022 | 1.149 |
| 16 | 1088.74 | 52.213 | 6.901 | 1092.6 | 1079.1 | 3.184 | 0.384 |
| 17 | 1134.07 | 49.213 | 18.5 | 1149.5 | 1117.67 | 7.606 | 2.197 |
| 18 | 1184.21 | 43.987 | 14.735 | 1192.89 | 1167.82 | 6.986 | 1.478 |
| 19 | 1231.46 | 47.604 | 18.497 | 1240.14 | 1219.89 | 4.779 | 1.189 |
| 20 | 1286.43 | 57.637 | 8.729 | 1295.11 | 1264.25 | 5.863 | 0.921 |
| 21 | 1341.4 | 30.649 | 29.017 | 1365.51 | 1319.22 | 15.388 | 4.967 |
| 22 | 1388.65 | 52.037 | 5.497 | 1402.15 | 1380.94 | 5.435 | 0.436 |
| 23 | 1412.76 | 54.821 | 10.116 | 1439.76 | 1403.12 | 7.015 | 0.86 |
| 24 | 1455.19 | 58.843 | 17.492 | 1479.3 | 1440.73 | 7.058 | 2.038 |
| 25 | 1493.77 | 43.207 | 17.312 | 1500.52 | 1480.26 | 5.28 | 1.265 |
| 26 | 1510.16 | 40.466 | 20.606 | 1532.34 | 1501.48 | 7.184 | 1.532 |
| 27 | 1601.77 | 50.488 | 11.162 | 1628.77 | 1595.02 | 6.018 | 0.656 |
| 28 | 1685.67 | 30.987 | 24.121 | 1696.28 | 1658.74 | 12.274 | 3.293 |
| 29 | 1711.71 | 30.817 | 26.772 | 1763.78 | 1697.24 | 15.304 | 3.705 |
| 30 | 1493.77 | 78.709 | 11.339 | 2896.88 | 2839.99 | 3.188 | 0.809 |
| 31 | 2932.56 | 73.192 | 11.941 | 2949.92 | 2818.1 | 3.086 | 0.867 |
| 32 | 2968.24 | 65.122 | 14.263 | 2980.78 | 2949.92 | 3.972 | 1.014 |
| 33 | 3039.6 | 75.7 | 9.266 | 3051.18 | 3018.39 | 2.882 | 0.725 |
| 34 | 3410.88 | 47.146 | 49.476 | 3537.2 | 3215.11 | 32.724 | 27.376 |

FIG.1B

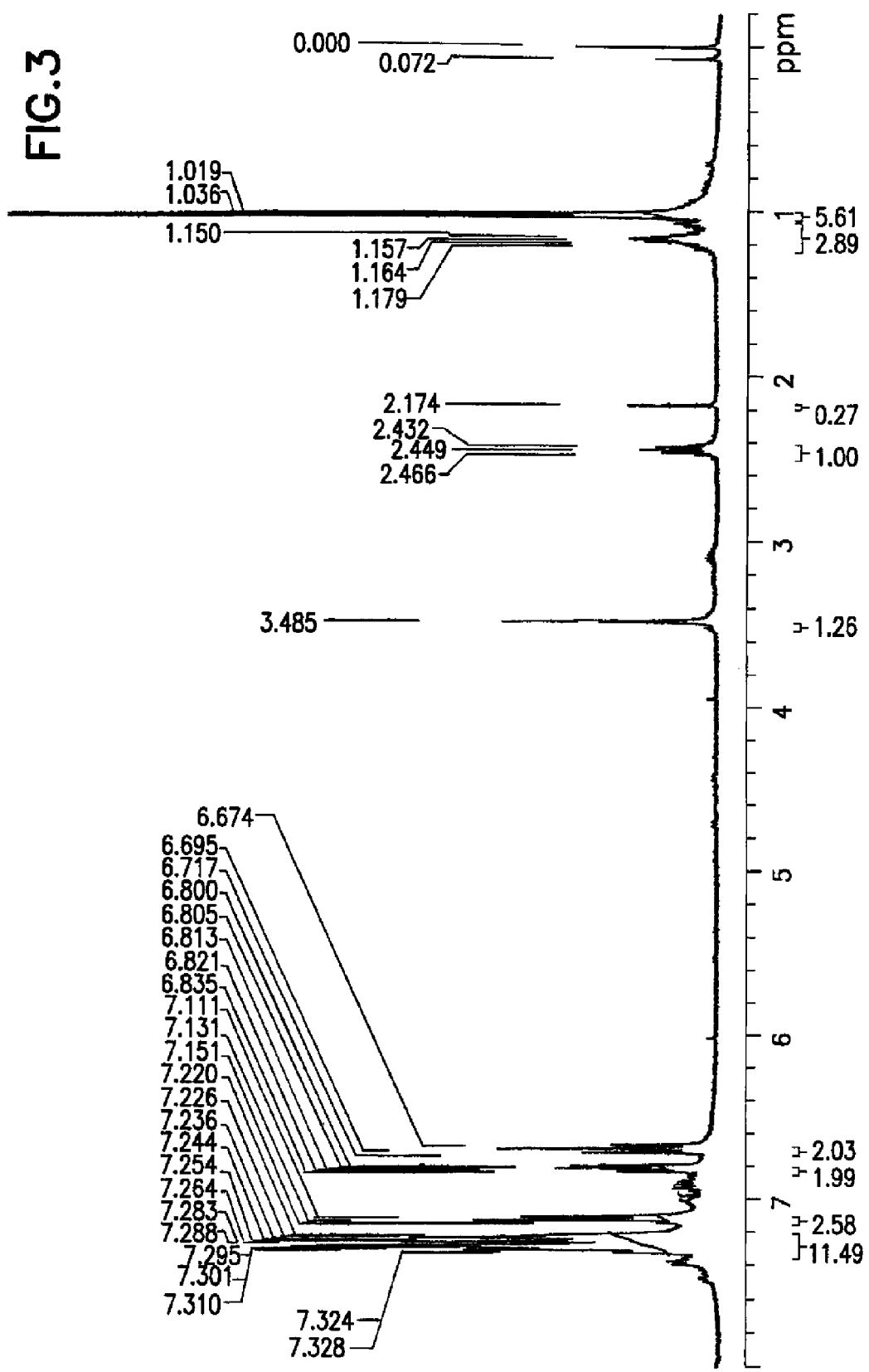

METHOD FOR THE PREPARATION OF 4-FLUORO-α-[2-METHYL-1-OXOPROPYL]-γ-OXO-N-β-DIPHENYLBENZENEBUTANAMIDE AND PRODUCTS THEREFROM

FIELD OF THE INVENTION

The present invention relates to a novel process for the preparation of 4-fluoro-α-[2-methyl-1-oxopropyl]-γ-oxo-N-β-diphenylbenzenebutanamide of the formula I, a key intermediate for the synthesis of Atorvastatin and isolation and characterization of an impurity formed during the preparation of 4-fluoro-α-[2-methyl-1-oxopropyl]-γ-oxo-N-β-diphenylbenzenebutanamide. The present invention in particular relates to an efficient and economical process for the preparation of 4-methyl-3-oxo-N-phenylpentamide for application in field of process chemistry of pharmaceutical drug substances.

BACKGROUND OF THE INVENTION 4-fluoro-α-[2-methyl-1-oxopropyl]-γ-oxo-N-β-diphenylbenzenebutanamide of formula I hereinafter referred to as DKT III, is a key intermediate for the synthesis of Atorvastatin

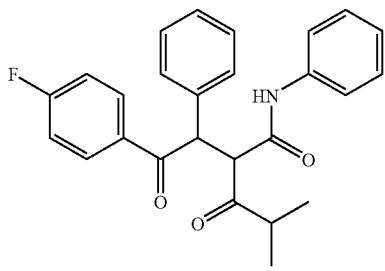

I

U.S. Pat. Nos. 4,681,893, 5,124,482, 5,216,174, 5,097,045 disclose the process for the preparation of Atorvastatin including the process for the preparation of compound of formula I by reacting 4-methyl-3-oxo-N-phenyl-2-(phenylmethylene)pentamide with 4-fluorobenzaldehyde in the presence of a catalyst such as 3-benzyl-5-(2-hydroxyethyl)-4-methylthiazolium chloride, 3,4-dimethyl-5-(2-hydroxyethyl)-thiazolium iodide, 3-ethyl-4-(2-hydroxyethyl)-4-methylthiazolium bromide, thiamine hydrochloride and the base selected from N,N-diisopropylethylamine, pyridine, N,N-dimethylamine, triethylamine, 1,8-diazabicyclo[5.4.0]undec-7-ene, 4-dimethylaminopyridine, N,N,N',N'-tetramethylethylenedimine.

WO03/004457 discloses the process for making 4-fluoro-α-[2-methyl-1-oxopropyl]-γ-oxo-N-β-diphenylbenzenebutanamide by reacting 2-bromo-1-(4-fluorophenyl)-2-phenone (a compound of formula II) with 4-methyl-3-oxo-N-phenylpentamide (a compound of formula III) by using a highly polar solvent system comprising DMF, ethanol and methanol. Product is isolated by precipitation with solvent like n-hexane. The remaining soluble material is recovered by chromatographic separation. The compound is obtained as diastereoisomeric mixture in a ratio of about 3:1 to 4:1 including unknown impurities. In case of mixture of ratio 3:1 and 4:1 the yield of DKT III is 75% and 80% respectively and the other impurity constituents of the remaining 20-25% mixture have neither been isolated nor characterized.

WO03/004457

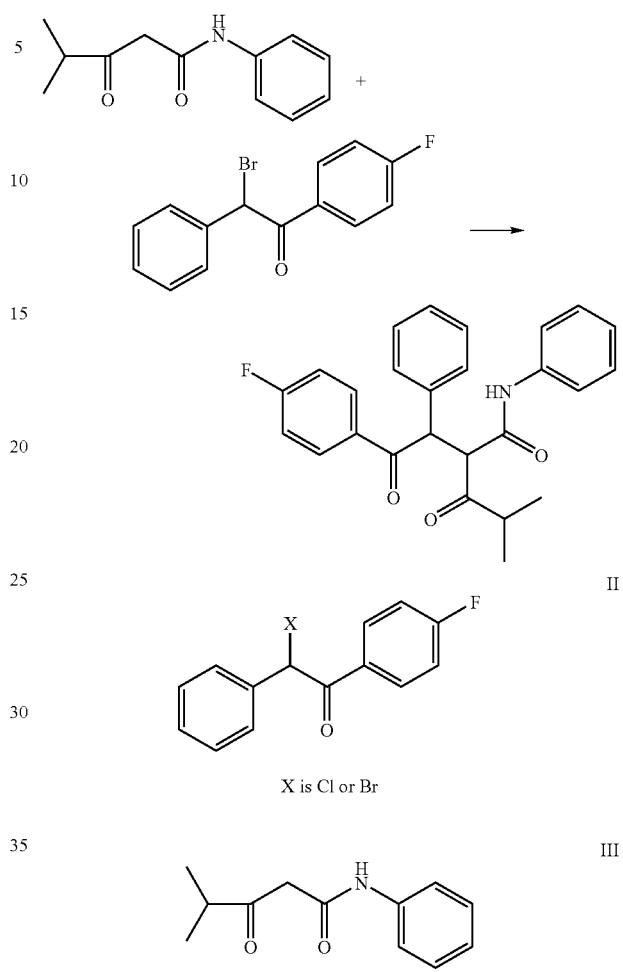

II

X is Cl or Br

III

Following schematic representation depicts different synthetic schemes for the preparation of compound of the formula I according to the references cited hereinbefore or after.

U.S. Pat. No. 5,124,482:

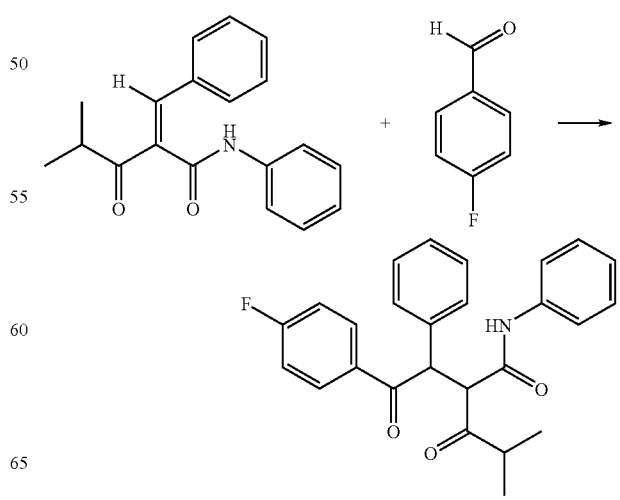

WO2006/021968:

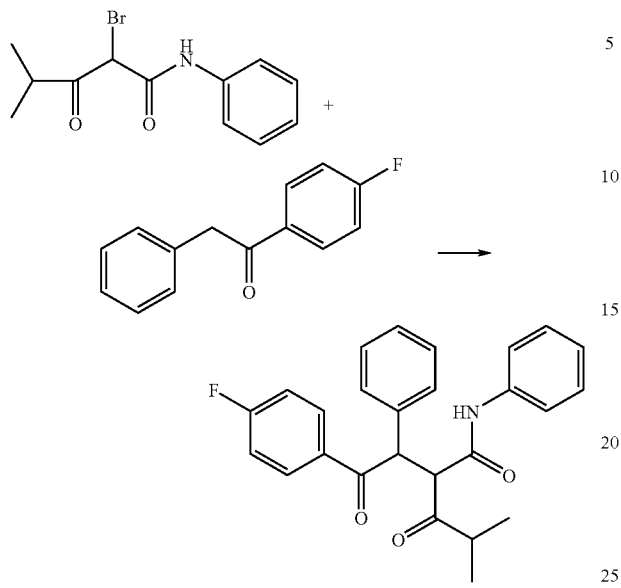

The compound of formula III was described in JOC, 1978, 43, 2087-2088, Synthesis 1992, 1213-1214, Chem. Pharm. Bull. 1987, 35, 1860-1870

WO2006/021968, discloses a process for DKT III comprising a reaction between bromo-4-methyl-3-oxo pentanoic acid phenylamide and 1-(4-fluoro phenyl)-2-phenyl ethanone. It discloses α-[2-methyl-1-oxopropyl]-γ-oxo-N-β-diphenylbenzene butanamide of formula IV hereinbefore and hereinafter referred as desfluoro and difluoro-α-[2-methyl-1-oxopropyl]-γ-oxo-N-β-diphenylbenzene butanamide of formula V hereinbefore and hereinafter referred as difluoro as impurities. It neither isolates nor characterizes any other impurity.

Other relevant references may include: KR 10-2004-0001435, J. Labelled Cpd. Radiopharm. 42, 121-127,1999, and KR 20050124322.

U.S. Pat. No. 5,216,174 discloses the preparation of 4-Methyl-3-oxo-N-phenylpentamide of formula III by reacting Methyl 4-methyl-3-oxopentaonate with aniline in toluene as a solvent in the presence of ethylene diamine as a base. The product is isolated after 10 days in 69% yield. WO200304457 also prepares a compound of formula III in accordance with the process of U.S. Pat. No. 5,216,174.

Purity of Atorvastatin is dependent on the purity of DKT III, it is, therefore, important to control impurities at this stage. Prior art reports desfluoro and difluoro as impurities that affect the purity of Atorvastatin, J. Labelled Cpd. Radiopharm. 42,121-127,1999 discloses that the presence of trace amounts of water during the synthesis of DKT III results in the formation of α-[2-methyl-1-oxopropyl]-γ-oxo-N-β-diphenylbenzene butanamide hereinbefore and hereinafter referred as desfluoro of formula IV as a major impurity; prior art also discloses the formation of difluoro-α-[2-methyl-1-oxopropyl]-γ-oxo-N-β-diphenylbenzene butanamide hereinbefore and hereinafter referred as difluoro of formula V as an impurity during the formation of DKT III.

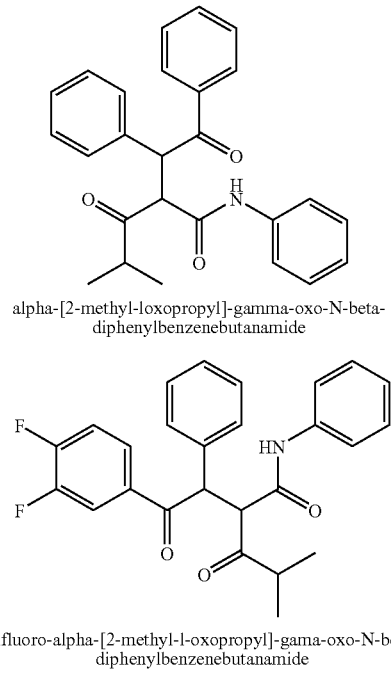

alpha-[2-methyl-1oxopropyl]-gamma-oxo-N-beta-diphenylbenzenebutanamide difluoro-alpha-[2-methyl-l-oxopropyl]-gama-oxo-N-beta-diphenylbenzenebutanamide The present invention discloses a process for preparing DKT III in 99:1 diastereoisomeric mixture comprising up to 1% total impurities with the desfluoro impurity of about 0.1% and the difluoro impurity about 0.05%. The invention also provides a process for the isolation and characterization of unknown impurity formed during the formation of DKT III. The newly characterized impurity is of formula VI and is up to 0.1%.

Prior art also discloses a process for making 4-Methyl-3-oxo-N-phenylpentamide of formula III that requires 10 days for the isolation of the product and is carried out in a solvent. The present invention discloses a process for making 4-Methyl-3-oxo-N-phenylpentamide of formula III which does not require any solvent and product is isolated in a single day reducing the reaction time 10 folds thus making it more efficient and economical.

During the preparation of DKT III comprising reaction between compounds of formula II & III, there exists a possibility of formation of compounds of formulae VI, VII. This could be based on the fact that compound of formula III possesses tautomerism and also exists as enol form as shown below.

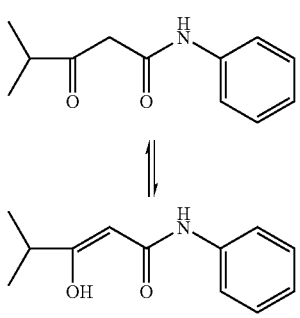

However compound of the formula VII as depicted below is enol form of DKT III. Keto enol forms always exist as equilibrium mixtures and it is impossible to isolate either of them in pure form. Therefore formation of VII as an impurity during the preparation of DKT III is forbidden. The existence of keto and enol form can be observed only by the spectroscopic techniques such as NMR.

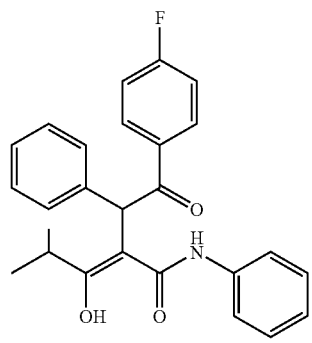

VII

Therefore probable impurity in DKT III due to the existence of enol form is 3-[2-(4-Fluorophenyl)-2-oxo-1-phenyl-ethoxy]-4-methyl-pent-2-enoic acid phenylamide hereinabove and hereinbelow referred to as O-alkylated impurity, of formula VI

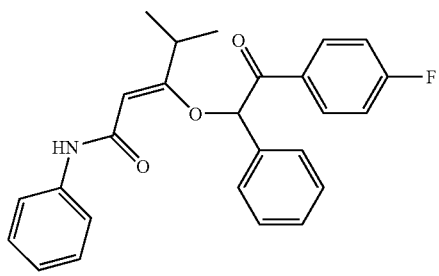

VI

Though O-alkylated is not listed in the prior art of DKT III and Atorvastatin, it is nevertheless important to minimize it in DKT III in the interest of higher purity and good yield of Atorvastatin.

In the present invention, inventors have studied and revealed that O-alkylation of enol tautomer to form O-alkylated impurity of formula VI affect the purity and yield of DKT III considerably.

OBJECT OF THE INVENTION

It is an object of the present invention to provide an improved process for the synthesis of the atorvastatin intermediate 4-fluoro-α-[2-methyl-1-oxopropyl]-γ-oxo-N-β-diphenylbenzenebutanamide.

It is another object of the present invention to provide an improved process for the synthesis of the atorvastatin intermediate 4-fluoro-α-[2-methyl-1-oxopropyl]-γ-oxo-N-β-diphenylbenzenebutanamide that is substantially free of impurities.

It is a further object of the present invention to provide an improved process for the synthesis of the atorvastatin intermediate 4-fluoro-α-[2-methyl-1-oxopropyl]-γ-oxo-N-β-diphenylbenzenebutanamide with O-alkylated impurity of about 0.1% or less.

It is yet another object of the present invention to provide an improved process for the synthesis of the atorvastatin intermediate 4-fluoro-α-[2-methyl-1-oxopropyl]-γ-oxo-N-β-diphenylbenzenebutanamide with high yield and purity.

It is yet another object of the present invention to provide 3-[2-(4-Fluorophenyl)-2-oxo-1-phenyl-ethoxy]-4-methyl-pent-2-enoic acid phenylamide (hereinafter referred to as O-alkylated impurity, shown as formula VI).

It is a further object of the present invention to synthesize atorvastatin in high yield and purity employing the intermediate 4-fluoro-α-[2-methyl-1-oxopropyl]-γ-oxo-N-β-diphenylbenzenebutanamide with O-alkylated impurity of about 0.1% or less.

It is another object of the present invention to provide a process for the synthesis of compound of Formula III.

It is another object of the present invention to isolate and characterize unknown impurities of DKT III.

SUMMARY OF THE INVENTION

According to an aspect of the present invention there is provided an improved process for synthesis of DKT III of formula I comprising step:

Reacting a compound 2-halo-1-(4-fluorophenyl)-2-phenone of formula II with 4-methyl-3-oxo-N-phenylpentamide of formula III in the presence of a base in C3-C5 alcohol as a solvent wherein the said compound of formula I is of high purity and good yield with total impurity of about 1%.

According to another aspect of the present invention there is provided a process for preparation of compound of formula III comprising the step of reaction of Methyl 4-methyl-3-oxopentaonate and aniline in presence of an organic base without using any solvent in good yield and the product being isolated in a single day.

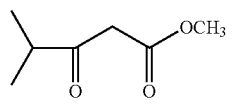

Methyl 4-methyl-3-oxopentaonate and

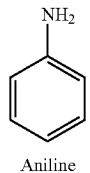

Aniline

According to another aspect of the present invention there is provided a process for the synthesis of atorvastatin with a yield of about 70% or greater comprising the step of reaction of the said compound of Formula I.

BRIEF DESCRIPTION OF ACCOMPANYING FIGURES

Figure 2:
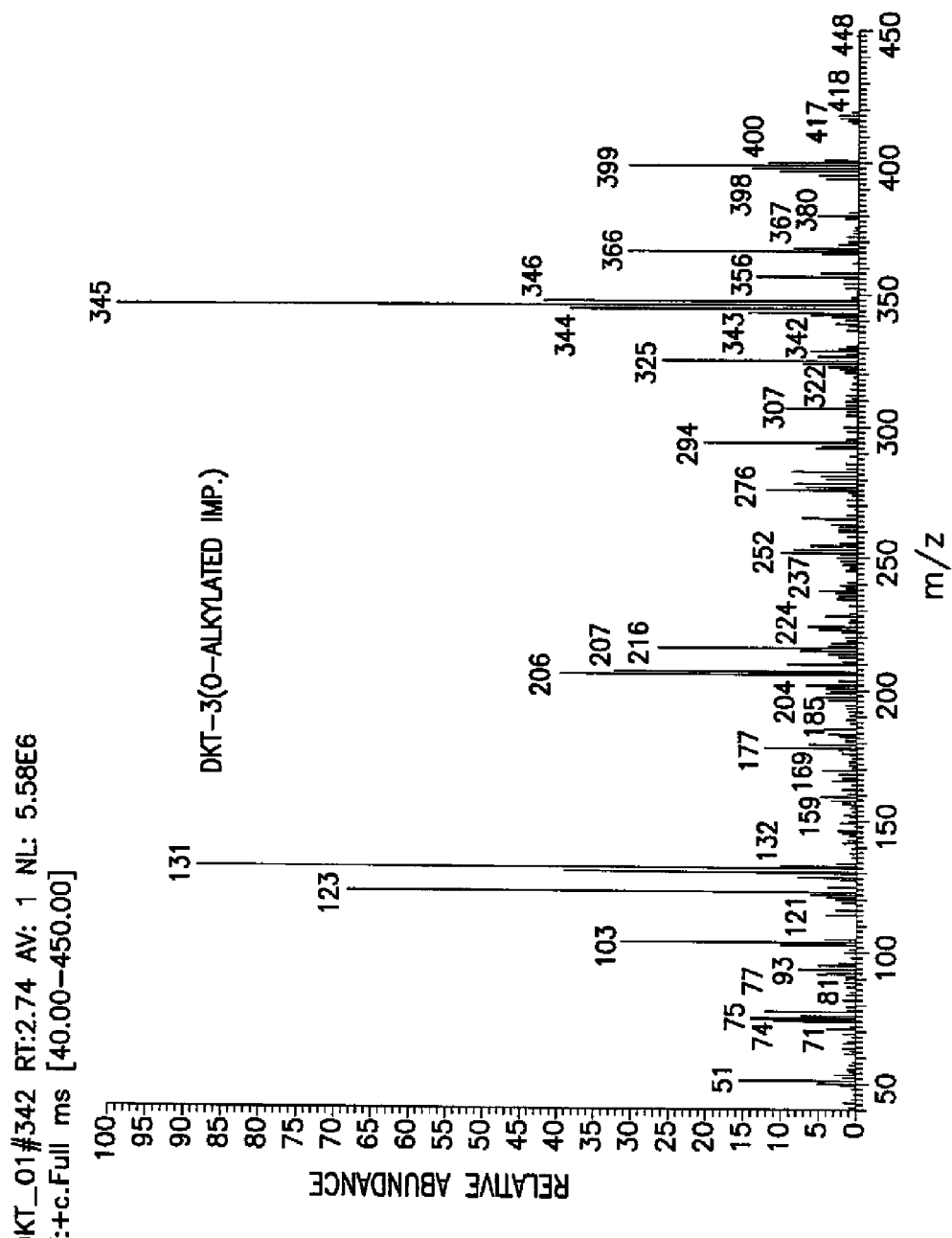

FIG. 1: Infra red spectrum for compound of formula VI
FIG. 2: Mass spectra for compound of formula VI FIG. 3: Proton Magnetic Resonance spectra for compound of formula VI

DETAILED DESCRIPTION OF THE INVENTION

Unless indicated to the contrary, the general and specific terms of the molecules and reaction conditions used hereinabove and hereinbelow preferably have the following meanings:

DKT III is 4-fluoro-α-[2-methyl-1-oxopropyl]-γ-oxo-N-β-diphenylbenzenebutanamide of formula I O-Alkylated is 3-[2-(4-Fluorophenyl)-2-oxo-1-phenyl-ethoxy]-4-methyl-pent-2-enoic acid phenylamide of formula VI Enol form of DKT III is 3-[2-(4-Fluorophenyl)-2-oxo-1-phenyl-ethyl]-3-hydroxy-4-methyl-pent-2-enoic acid phenylamide of formula VII.

Desfluoro is a-[2-methyl-1-oxopropyl]-γ-oxo-N-β-diphenylbenzenebutanamide

Difluoro is α-[2-methyl-1-oxopropyl]-γ-oxo-N-β-diphenylbenzenebutanamide

Halogen means chlorine, bromine or iodine

C3-C5 alkyl group can be linear or can be branched.

The present invention provides a novel process for making 4-fluoro-α-[2-methyl-1-oxopropyl]-γ-oxo-N-β-diphenyl-benzenebutanamide of formula I which in turn can be used for making Atorvastatin with an improved impurity profile and isolation and characterization of an unknown new impurity. This invention also discloses a novel 10 times less time consuming method of making Methyl 4-methyl-3-oxopentaonate which is an intermediate for preparing DKT III compound of formula I.

The invention especially relates to a process for the preparation of a key intermediate for Atorvastatin, 4-fluoro-α-[2-methyl-1-oxopropyl]-γ-oxo-N-β-diphenylbenzenebutanamide of formula I

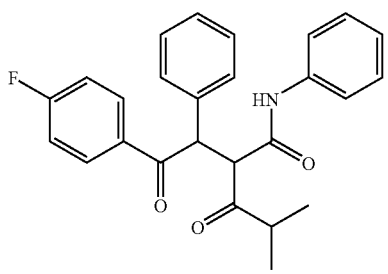

I

Obtained by nucleophilic substitution reaction of 2-halo-1-(4-fluorophenyl)-2-phenone compound of formula II

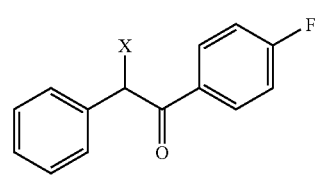

II

Wherein leaving halogen group X is Cl or Br, preferably Cl with methyl 4-methyl-3-oxopentaonate of formula III.

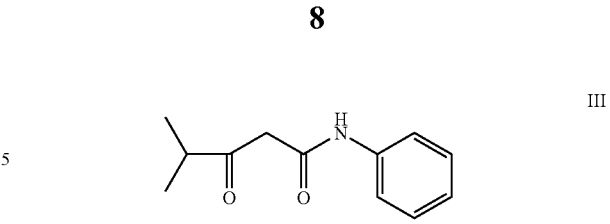

III

The process of the present invention in its first aspect is outlined in Scheme 1

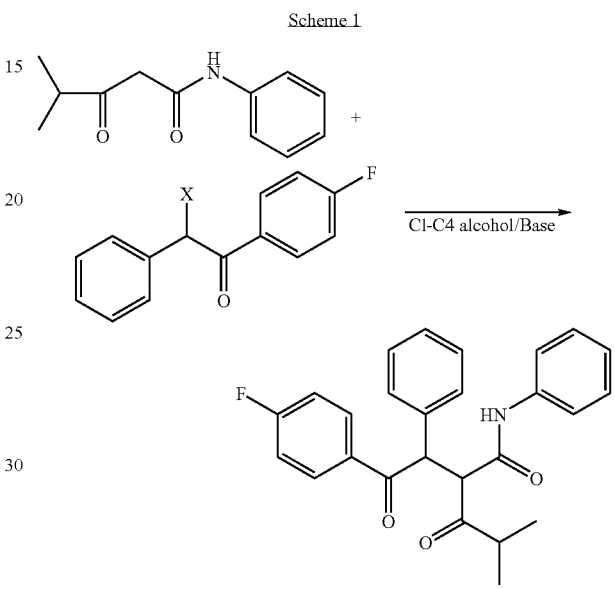

Scheme 1

X is Cl, Br or I; preferably X is Cl or Br. More preferably X is Cl.

The base may be inorganic or organic like sodium carbonate, potassium carbonate, cesium carbonate, diisopropylethylamine, triethylamine, lithium diisopropylamide, sodium hydride, n-butyl lithium, sodium ethoxide, metal hydroxide, or a mixture thereof.

WO2003004457 discloses the preparation of 4-fluoro-α-[2-methyl-1-oxopropyl]-γ-oxo-N-β-diphenylbenzenebutanamide by reacting 2-bromo-1-(4-fluorophenyl)-2- with 4-methyl-3-oxo-N-phenylpentamide in a polar solvents or solvent mixture or polar aprotic solvents especially Ethanol or Methanol or DMF. It is reported that when the reaction is carried out in DMF the product is a mixture of diastereoisomers in the ratio of 3:1 indicating 25% impurities. When the same reaction is carried out in methanol the product contains about 50% impurities.

Disclosed herein is an improved process for making 4-fluoro-α-[2-methyl-1-oxopropyl]-γ-oxo-N-β-diphenyl-benzenebutanamide by reacting 2-bromo-1-(4-fluorophenyl)-2- with 4-methyl-3-oxo-N-phenylpentamide in an organic solvent in the presence of a base. Process of this invention gives the DKT III in at least 70% yield with total impurities about 1%.

The organic solvent is C3-C5 alcohol. Preferably organic solvent is selected from n-propanol, isopropanol, n-butanol, iso-butanol, t-butanol, n-pentanol, iso pentanol, t-pentanol, a mixture thereof. More preferably organic solvent is isopropanol.

The base may be inorganic or organic like sodium carbonate, potassium carbonate, cesium carbonate, diisopropylethylamine, triethylamine, lithium diisopropylamide, sodium hydride, n-butyl lithium, sodium ethoxide, metal hydroxide, or a mixture thereof. The organic solvent comprises Methylethylketone, Methylisobutylketone, Dichloromethane, Methanol, ethanol and the like and mixture thereof.

Also disclosed herein is a process for making Atorvastatin. DKT III of the present invention on reaction with (4R-cis)-1, 1-dimethylethyl-6-(2-aminomethyl)-2,2-dimethyl-1,3-dioxane-4-acetate in presence of pivalic acid in cyclohexane as solvent results in the formation of (4R-cis)-1,1-dimethylethyl-6-{2[2-fluorophenyl]-5-(1-methylethyl)-3-phenyl-4-[(phenylamino) carbonyl]-1H-pyrrol-1-yl]}-2,2-dimethyl-1, 3-dioxane-4-acetate. This compound on hydrolysis is converted into sodium salt which is then further converted into Atorvastatin calcium by the process available in the literature.

Impurities are about 0.1% α-[2-methyl-1-oxopropyl]-γ-oxo-N-β-diphenylbenzenebutanamide (hereinabove and hereinbelow referred as Desfluoro of Formula IV), about 0.05% difluoro α-[2-methyl-1-oxopropyl]-γ-oxo-N-β-diphenylbenzenebutanamide (hereinabove and hereinbelow referred as difluoro of Formula V) and about 0.01% 3-[2-(4-Fluorophenyl)-2-oxo-1-phenyl-ethoxy]-4-methyl-pent-2-enoic acid phenylamide (hereinabove and hereinbelow referred to as O-alkylated of Formula VI).

4-methyl-3-oxo-N-phenylpentamide may exist in tautomeric forms as shown below:

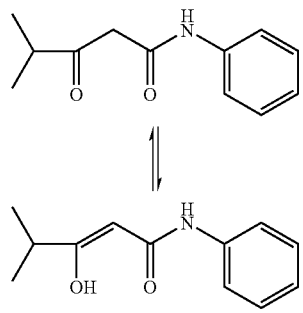

There is a probability that the other reactant used for the formation of DKT III, halo-1-(4-fluorophenyl)-2-phenone of formula II can form any of the following 2 compounds of formulas VI and VII:

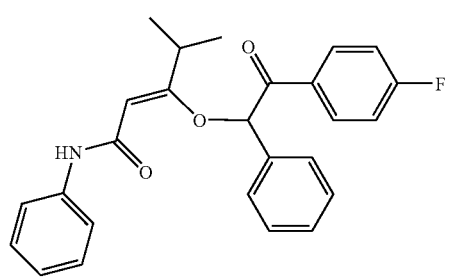

(O-Alkylated Impurity)

The compound of formula VI is 3-[2-(4-Fluorophenyl)-2-oxo-1-phenyl-ethoxy]-4-methyl-pent-2-enoic acid phenylamide which is formed as a result of ether formation of the enolic tautomeric form of 4-methyl-3-oxo-N-phenylpentamide and hereinbefore and hereinabove and herein below referred as O-alkyl impurity.

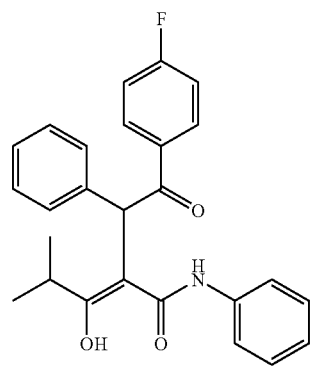

Enol form of DKT III

In an embodiment the reaction between 4-methyl-3-oxo-N-phenylpentamide of formula III and halo-1-(4-fluorophenyl)-2-phenone of formula II is carried out in methanol as a solvent in the presence of an inorganic base. The yield of DKT III is lower and the impurities formed are about 50%. The impurities are Desfluoro, Difluoro and O-Alkylated and major impurity is O-Alkylated.

In a preferred embodiment the reaction between 4-methyl-3-oxo-N-phellylpentamide of formula III and halo-1-(4-fluorophenyl)-2-phenone of formula II is carried out in acetone as a solvent using the same base and under same set of reaction conditions as for methanol as solvent. The yield of DKT III is lower and the impurities formed are about 25%. The impurities are Desfluoro, Difluoro and O-Alkylated and major impurity is O-Alkylated.

In a especially preferred embodiment the reaction between 4-methyl-3-oxo-N-phenylpentamide of formula III and halo-1-(4-fluorophenyl)-2-phenone of formula II is carried out in isopropanol as a solvent using the same base and under same set of reaction conditions when methanol, acetone or DMF is used as a solvent.

The DKT III is purified and isolated from isopropyl alcohol, methylene dichloride/hexane, ethyl acetate/hexane, or a mixture thereof. Preferably DKT III is purified and isolated from a mixture of isopropanol and methanol.

The final product isolated from a mixture of isopropanol and methanol DKT III is obtained in at least 70% yield and the total impurities are up to 1%. Impurities are desfluoro about 0.1%, difluoro about 0.05% and O-Alkylated about 0.1%.

The present invention discloses isolation and characterization of a new compound from the product mixture of reaction between 4-methyl-3-oxo-N-phenylpentamide of formula III and halo-1-(4-fluorophenyl)-2-phenone of formula II to form DKT III which has been referred hereinabove and hereinbelow as O-Alkylated impurity of formula VI.

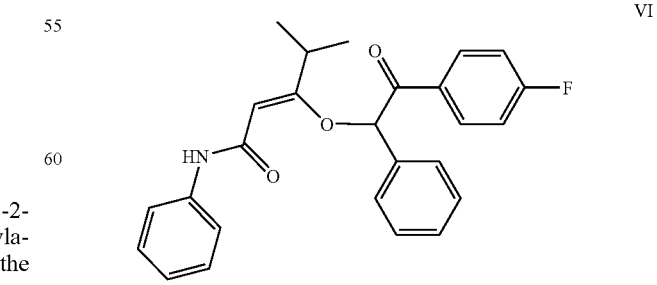

O-Alkylated impurity has been isolated and purified by traditional techniques such as column chromatography, crystallisation, preparative TLC and the like. It has been characterized by spectroscopic techniques such as IR, UV, Mass, NMR, and the like.

Mass spectroscopy of O-Alkylated impurity: DI-MS: 418, 417,399, 366, 345,325, 294, 276, 252, 216, 206, 177, 131, 123, 93, 77, 103. $M^{+1}$ at 418 and $M^+$ at 417 in mass spectroscopic analysis of impurity indicates that it contains both the reactant moieties 4-methyl-3-oxo-N-phenylpentamide of formula III and halo-1-(4-fluorophenyl)-2-phenone of formula II, therefore is an isomer of DKT-III.

Infra red spectrum (KBr)of DKT-III: 1720 $cm^{-1}$, 1681 $cm^{-1}$ and 1647 $cm^{-1}$ represent 3 carbonyl groups in DKT III molecule. Infrared spectra of O-Alkylated impurity have 1685 $cm^{-1}$ and 1711 $cm^{-1}$ representing 2 carbonyl groups., 1601 $cm^{-1}$ represent C=C stretching conjugated with C=O=1231 $cm^{-1}$ represents ether group in the molecule.

1H-NMR (400 MHZ, CDCl3): 1.027(2H, d, J=6.8 HZ), 2.174 (1H,s,), 2.449 (1H.m), 3.485 (1H,s), 6.674-7.328(14H, m).2 singlet proton NMR values at 2,174 and 3.485 represent methine and olefinic protons respectively which are characteristic for O-Alkylated impurity.

In another aspect this invention discloses a novel process for the preparation of 4-methyl-3-oxo-N-phenylpentamide in good yield with reaction time is significantly shortened by 10 times. This process makes the Atorvastatin production economical and environmental friendly on an industrial scale.

The process of the present invention in this aspect is outlined in Scheme II

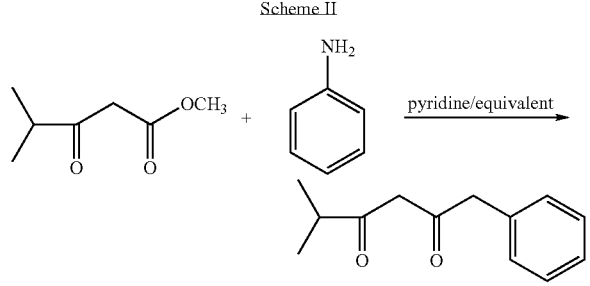

Scheme II

In an embodiment 4-Methyl-3-oxo-pentaonate is taken in a in a liquid base without any solvent, such as pyridine, picolines, lutidines halogenated pyridines and the like. The reaction contents are heated and aniline is added in about 30 minutes to about 4 Hrs. The reaction gets completed in 2-6 Hrs. The liquid base and methanol produced as a byproduct are removed by distillation and the reaction contents are cooled and pH adjusted to about 0.5 to about 2.On cooling about 99% pure 4-Methyl-3-oxo-N-phenylpentamide of formula III in about 75% yield is obtained. The product is obtained in a single day compared to if the process is carried out in accordance with U.S. Pat. No. 5,216,174 wherein the product is isolated in 10 days.

The following non limiting examples will illustrate the invention clearly.

Preparation of 4-fluoro-α-[2-methyl-1-oxopropyl]-γ-oxo-N-β-diphenylbenzenebutanamide

EXAMPLE 1

The mixture containing 300 ml isopropanol and 100 g of the formula III is cooled to 10-15° C. Potassium carbonate 94 g is charged into the above contents keeping the temperature 10-15° C. A solution of 128 gm of formula II in 125 ml isopropanol is then added slowly in 2-3 hrs keeping temperature at 10-15° C. Temperature is allowed to reach at 25-30° C. Temperature is further raised to 40-45° C. and then maintained for 8-10 hrs with simultaneous monitoring on HPLC. After HPLC complies, isopropanol is removed under vacuum keeping temperature below 55° C. followed by the addition of 600 ml ethyl acetate at 40-45° C. 600 ml water is charged and the organic layer is collected. Solvent is removed under vacuum when a solid mass is seen. This solid is purified by using isopropanol and methanol. Purity 99.69% with 0.047% of DESFLUORO impurity, Difluoro almost nil and O-alkylated impurity to be 0.1% with yield of 73%.

EXAMPLE 2

The mixture containing 88 ml t-butyl alcohol and 29 g of the formula III is cooled to 10-15° C. Potassium carbonate 27 g is charged into the above contents keeping the temperature 10-15° C. A solution of 36 gm of formula II in 35 ml t-butyl alcohol is then added slowly in 2-3 hrs keeping temperature at 10-15° C. Temperature is allowed to reach at 25-30° C. Temperature is further raised to 40-45° C. and then maintained for 8-10 hrs with simultaneous monitoring on HPLC. After HPLC complies, t-butanol is removed under vacuum keeping temp below 55° C. followed by the addition of 175 ml ethyl acetate at 40-45° C. 175 ml water is charged and the organic layer is collected. Solvent is removed under vacuum when a solid mass is seen. This solid is then purified by using isopropanol and methanol. Resulting purity found to be 99.5% with 0.042% of Desfluoro impurity, Difluoro almost nil and O-alkylated impurity to be 0.12% with yield of 35 g.

EXAMPLE 3

The mixture containing 300 ml methanol and 100 g of the formula III is cooled to 10-15° C. Potassium carbonate 94 g is charged into the above contents keeping the temperature 10-15° C. A solution of 128 gm of formula II in 125 ml methanol is then added slowly in 2-3 hrs keeping temperature at 10-15° C. Temperature is allowed to reach at 25-30° C. Temperature is further raised to 40-45° C. and then maintained for 8 hrs with simultaneous monitoring on HPLC. HPLC revealed the progress of the reaction to be 39%, unreacted compound of formula III to be 46.0% and O-alkylated impurity to be 7.9%. Looking at the unreacted starting material of formula III, compound 11 is further added and reaction is pursued but it results in enhancing the O-alkylated impurity.

EXAMPLE 4

The mixture containing 300 ml acetone and 100 g of the formula III is cooled to 10-15° C. Potassium carbonate 94 g is charged into the above contents keeping the temperature 10-15° C. A solution of 128 gm of formula II in 125 ml acetone is then added slowly in 2-3 hrs keeping temperature at 10-15° C. Temperature is allowed to reach at 25-30° C. Temperature is further raised to 40-45° C. and then maintained for 8 hrs with simultaneous monitoring on HPLC. HPLC revealed the progress of the reaction to be 65%, unreacted compound of formula III to be 10.0%, 8.1% of formula II and O-alkylated impurity to be 14.7%. Looking at the unreacted starting material reaction is pursued but it results in enhancing the O-alkylated impurity.

Preparation of (4R-cis)-1,1-dimethylethyl-6-{2[2-fluorophenyl)-5-(1-methylethyl)-3-phenyl-4-[(phenylamino)carbonyl]-1H-pyrrol-1-yl]}-2,2-dimethyl-1,3-dioxane-4-acetate

EXAMPLE 5

58 g (4R-cis)-1,1-dimethylethyl-6-(2-aminomethyl)-2,2-dimethyl-1,3-dioxane-4-acetate is charged with 480 ml of cyclohexane at RT followed by the addition of 84 g of DKT III and 12 g of pivalic acid at RT. The reaction mass is heated to reach at 78° C. and water is removed azeotropically. Reaction is maintained for 62 hrs and is monitored. After the completion, reaction mass is quenched with sodium bicarbonate solution. Organic layer separated is washed thoroughly till it is free from acidity. Cyclohexane from the organic layer is recovered under vacuum. Residue so obtained is dissolved in isopropanol and product is isolated by the addition of water at 30-35° C. Product is further purified from isopropanol.

Preparation of Atorvastatin Calcium

EXAMPLE 6

40.0 g (4R-cis)-1,1-dimethylethyl-6-{2[2-fluorophenyl)-5-(1-methylethyl)-3-phenyl-4-[(phenylamino)carbonyl]-1H-pyrrol-1-yl]}-2,2-dimethyl-1,3-dioxane-4-acetate is taken into 641 ml methanol. Heat the contents to 45-50° C. till it gives a clear solution. Add 10.0 g at 20-26° C. of hydrochloric acid. Reaction is maintained for 6 hrs., reaction is monitored on HPLC. After complete conversion it is added with solution of 7.0 g NaOH dissolved in 65 ml water at 23-26° C. till the pH of 12-12.5 is reached. Contents are slowly heated to reach at 35-40° C. and then maintained for 6 hrs. Completion of the reaction is followed by concentration of reaction mass under vacuum. Concentrated mass thus obtained is diluted with aqueous methanol and extracted with methyl tert butyl ether at 30-32° C. Aqueous layer is collected and given the washing with mixture containing n-hexane and cyclohexane (1:1v/v).pH of aqueous layer is adjusted to 8.2-8.4 using sodium hydroxide solution at 30-32° C. Finally calcium acetate 6.0 g dissolved in 194 ml water is added to aqueous at 47-50° C. till turbidity is observed. Contents are further heated till salt is precipitated. Product is filtered off and dried.

Preparation of 4-methyl -3-oxo-N-phenylpentamide

EXAMPLE 7

Reaction mixture containing 100 g methyl isobutyryl acetate and 100 ml of pyridine is heated at temperature of 110-115° C. 77.5 g aniline is added slowly in about two hrs keeping reaction mass at 110-115° C. for 12 hrs. Completion of the reaction is monitored by TLC. Mixture of pyridine and methanol is distilled out at 85-90° C. under reduced pressure. Contents are cooled to 35-40° C. and water is added followed by pH adjustment to 1-1.5. Mass is cooled further to 10-20° C. and product is filtered off. Wet cake obtained as 125-150 g (moisture content 20%, assay 98.5% by HPLC). Product is further dried to get 138 g product.

What is claimed is:
1. An improved process for the preparation of compound of Formula I

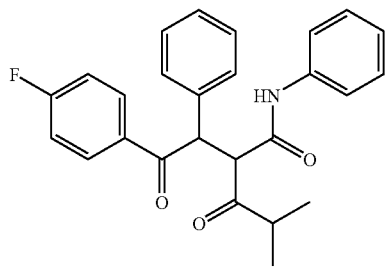

comprising reacting a compound of formula II

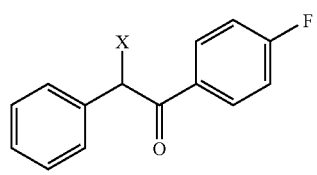

with a compound of formula III

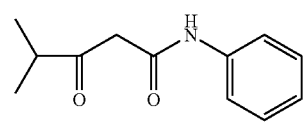

in C3-C5 alcohol as a solvent in the presence of a base;
wherein O-Alkylated impurity of formula VI in a compound of formula I
wherein the improvement comprises adding C3-C5 alcohol as a solvent in the presence of a base, and wherein, the compound of formula VI is formed as an impurity during the process of preparing compound of formula I

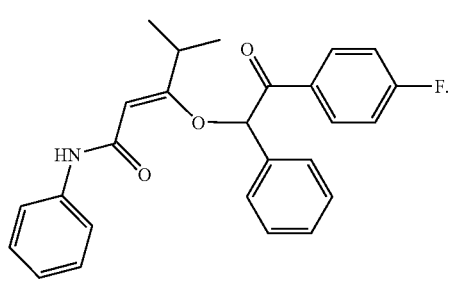

2. The process for preparation of compound of formula I as claimed in claim 1 wherein the solvent is selected from n-butanol, isobutanol, t-butanol, n-propanol, isopropanol or a mixture thereof.

3. The process for preparation of compound of formula I as claimed in claim 2 wherein the solvent is isopropanol.

4. The process for preparation of compound of formula I as claimed of claim 1 wherein the base may be inorganic or organic and selected from a group consisting of sodium carbonate, potassium carbonate, cesium carbonate, diisopropylethylamine, triethylamine, lithium diisopropylamide, sodium hydride, n-butyl lithium, sodium ethoxide, metal hydroxide, or a mixture thereof.

5. A process of claim 1 wherein impurities in compound of formula I are α-[2-methyl-1-oxopropyl]-γ-oxo-N-β-diphenylbenzenebutanamide of formula IV up to 0.1%; α-[2-methyl-1-oxopropyl]-γ-oxo-N-β-diphenylbenzenebutanamide of formula V up to 0.05% and 3-[2-(4-Fluorophenyl)-2-oxo-1-phenyl-ethoxy]-4-methyl-pent-2-enoic acid phenylamide of formula VI up to 0.1%

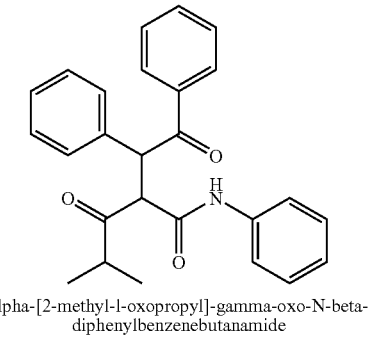

alpha-[2-methyl-1-oxopropyl]-gamma-oxo-N-beta-diphenylbenzenebutanamide

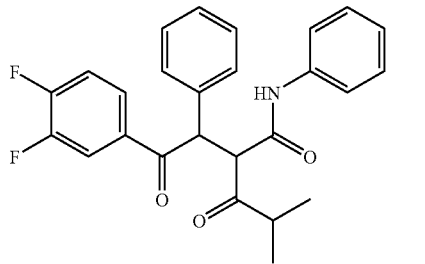

difluoro-alpha-[2-methyl-1-oxopropyl]-gamma-oxo-N-beta-diphenylbenzenebutanamide

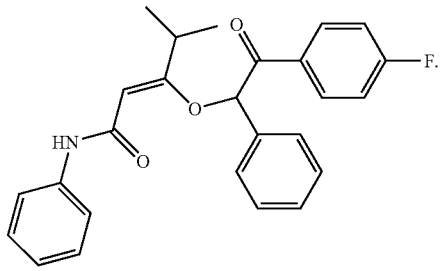

6. A process of claim 1 wherein the compound of formula I can be used to produce Atorvastatin in at least 70% yield.

* * * * *